(12) United States Patent
Freed

(10) Patent No.: US 6,216,570 B1
(45) Date of Patent: Apr. 17, 2001

(54) DRIVER FOR CAPTIVELY HOLDING A FASTENER DURING ASSEMBLY AND DISASSEMBLY OF TWO PARTS

(75) Inventor: Paul S. Freed, Bloomfield Hills, MI (US)

(73) Assignee: L. Vad Technology, Inc., Detroit, MI (US)

( * ) Notice: Subject to any disclaimer, the term of this patent is extended or adjusted under 35 U.S.C. 154(b) by 0 days.

(21) Appl. No.: 09/225,584

(22) Filed: Jan. 5, 1999

(51) Int. Cl.[7] ....................................................... B25B 23/14
(52) U.S. Cl. ................................................. 81/467; 81/476
(58) Field of Search .............................. 81/467, 451, 473, 81/475, 476

(56) References Cited

U.S. PATENT DOCUMENTS

| | | | |
|---|---|---|---|
| 243,885 | * | 7/1881 | Gulzow .................................... 81/476 |
| 857,632 | * | 6/1907 | Kihlgren ............................. 81/476 X |
| 1,876,990 | * | 9/1932 | Lormor .................................... 81/476 |
| 3,517,714 | * | 6/1970 | Desbarats ................................ 81/451 |
| 3,826,241 | | 7/1974 | Bucalo . |
| 4,004,298 | | 1/1977 | Freed . |
| 4,038,757 | * | 8/1977 | Hicks et al. ........................ 81/451 X |
| 4,106,373 | * | 8/1978 | Trongo ............................... 81/451 X |
| 4,321,914 | | 3/1982 | Begovac et al. . |
| 4,393,873 | | 7/1983 | Nawash et al. . |
| 4,526,072 | * | 7/1985 | Manhoff ................................. 81/451 |
| 4,581,020 | | 4/1986 | MacGregor . |
| 4,630,597 | | 12/1986 | Kantrowitz et al. . |
| 4,634,422 | | 1/1987 | Kantrowitz et al. . |
| 4,704,929 | * | 11/1987 | Osada .................................... 81/451 |
| 4,790,826 | | 12/1988 | Elftman . |
| 4,804,369 | | 2/1989 | Lapeyre et al. . |
| 4,897,081 | | 1/1990 | Poirier et al. . |
| 4,955,861 | | 9/1990 | Enegren et al. . |
| 5,098,397 | | 3/1992 | Svensson et al. . |
| 5,139,508 | | 8/1992 | Kantrowitz et al. . |
| 5,242,415 | | 9/1993 | Kantrowitz et al. . |
| 5,312,364 | | 5/1994 | Jacobs . |
| 5,387,192 | | 2/1995 | Glantz et al. . |
| 5,637,088 | | 6/1997 | Wenner et al. . |
| 5,833,655 | | 10/1998 | Freed et al. . |

* cited by examiner

Primary Examiner—James G. Smith
(74) Attorney, Agent, or Firm—Young & Basile, P.C.

(57) ABSTRACT

A percutaneous access device implantable beneath the skin of a patient includes a turret assembly containing current limiters, electrical contacts and fluid couplings and includes a sealing device having a small screw fastener at the bottom of the turret assembly. A screwdriver is provided configured to have access through a required air inlet passage to provide rapid removal and replacement of a new turret. The screwdriver includes a shaft having an eccentric drive socket. A handle has a roller clutch bearing pressed in place to allow the handle to freely turn clockwise to tighten the screw but locks the handle to the shaft for screw extraction in the counterclockwise direction. A driver captively engages a fastener for assembling a first part having a shoulder to a mating fitting having an aperture. The driver includes a shaft having a fastener-engaging end, and a mechanism, operably engageable between the shaft and the first part, for holding the fastener in a full forward position against the shoulder of the first part during attachment of the fastener to the aperture of the mating fitting.

6 Claims, 4 Drawing Sheets

DRIVER FOR CAPTIVELY HOLDING A FASTENER DURING ASSEMBLY AND DISASSEMBLY OF TWO PARTS

FIELD OF THE INVENTION

This invention pertains to a driver for captively holding a fastener during assembly and disassembly of two parts, and more particularly to percutaneous access devices employed to establish a connection through the skin between an organ or device implanted within the human body and an external device such as a monitor, pump or the like. More particularly, this invention pertains to means for accessing the electrical conduits as well as fluid conduits and mechanical connection features of the percutaneous access device.

BACKGROUND OF THE INVENTION

Percutaneous access devices hereinafter referred to as PAD, are employed to establish a connection projecting outward through the skin between an organ or a device implanted on a long term basis within the human body, and an external device such as a monitor, pump or the like. The PAD provides both mechanical and electrical access to the internal organs or devices and as such can be equipped with channels for conveying fluids or gases as well as electrical contacts for transmitting signals, for example, an ECG, or supplying power to devices. Such electrical contacts are usually partially exposed and could convey voltages and currents or become the grounding point for a substantial discharge of electricity generated in fabrics, carpets and the like.

For this reason it is necessary to install a current limiting device between the PAD contact and the organ or device, and this places the location of the limiter within the PAD (as a non-surgically renewable component). Because current limiters can fail, it is necessary that the limiters are positioned such that removal and replacement is possible without resorting to any surgery. Electrical contacts as well as fluid sealing surfaces and mechanical connection features also require periodic monitoring and maintenance since they are subject to everyday abrasion, abuse and actual breakage. The placement of electrical and/or mechanical devices in the PAD housing complicates the task of performing routine diagnostics and general troubleshooting and is limited by the permanent connection of the PAD to organs and devices requiring a carefully controlled operating or interrogating procedure.

A turret assembly containing the current limiters, electrical contacts and the fluid coupling and sealing device is used to render all of the components that are susceptible to breakdown and damage (except the implant body itself) to rapid removal and replacement by a fresh turret so that the PAD function is only momentarily disabled.

It is physiologically advantageous to use a PAD size consistent with sound implantation practices (minimal intrusion) and the ability to survive intact for long periods of time (conservative material mass). This severely limits the space and location available for a turret and requires the use of a small screw fastener at the bottom of the turret which must be accessed by a screwdriver working through the required air inlet passage which branches off just shy of the bottom.

It is desired to make the installation and lock down or removal of the turret as foolproof and rapid as possible, capable of accomplishment by a person of average skill. It is further desired to preclude a person from using tools or fasteners that are unsuitable. Further, it is desired to prevent a screwdriver of the wrong shape or size being applied to the screw head so that the drive slot or socket is damaged preventing removal of the turret. It is desired to prevent the fastener being overtorqued such that it is structurally compromised. It is desired to prevent the fastener prior to tightening, to shift in orientation or assume a position which makes the screwdriver engagement difficult or impossible. It is desired to prevent the wrong fastener being used which can jam into the threaded receiver of the PAD body and making turret removal very difficult. Further, it is desired to prevent excessive torque being applied to the fastener causing trauma to the PAD or skin interface.

A situation akin to the PAD example above, in which a turret or insert having a slenderness ratio of approximately 3 to 1 (length to diameter) or greater, is frequently encountered in mechanical and electromechanical assemblies. Oftentimes such a component is held into a base by means of a threaded fastener because it is only a threaded fastener that will provide great holding strength while occupying the smallest possible volume that makes lockdown of the part possible. Screws are also among the most economical of fasteners, are universally understood and are easily replaceable.

The installation and removal of such turrets is complicated by the difficulty of positioning the fastener drive tool so that it will engage the screw slot or drive socket. Visibility is usually very limited and may even be unattainable for deep turrets with small passages that access the screw, where the driver occupies most of the passage. Furthermore, the screw may be quite short in length and have a small head and not fall into the pilot diameter or clearance hole in the bottom of the turret. The turret may be a drawn can or a part with a thin bottom and simply having a clearance hole in lieu of any pilot hole. It can then become very difficult to probe for the fastener to get it to fall into place ready for driving. All this can become substantially more challenging if time is of the essence (a medical procedure), or if one is working upside down, for example, because the base (which could be a vehicle underside) cannot be strategically placed in a comfortable working position.

For these reasons, devices such as captive fasteners are sometimes used where the screw is disengaged from the base by turning but which cannot fall out of the turret clearance or pilot hole. The captive fastener is not an option for many assemblies due to considerations of space, cost and strength. These captive fasteners can still misalign because they are inherently free to mutate in the clearance hole. One common variant of such fastener devices involves relieving the threads adjacent to the head so that the screw may be threaded into a tapped hole in the bottom of the turret and fall into place and be captivated when the relief diameter is reached. This fastener scheme is limiting in application because it is usually desired to push the turret into the socket or housing prepared for it in the base so that it bottoms out and in some cases keys in place for the proper orientation. To accomplish this with a relieved screw requires that the screw be able to slide up into the turret so it does not interfere with seating or that it fit into a counterbore in the housing for the same reason. Both solutions mandate more depth of material and lead to increasing the overall size of the assembly. In the case of very tiny screws, i.e. No. 1 and smaller, thread relief becomes a difficult and expensive option because most screws are produced by thread rolling and will require post machining.

Yet another option is to push the turret into position and screw it down by holding the screw in a locking or magnetized (ferrous screws) driver. Such drivers frequently fail to hold the fastener properly leading to cross threading and possible thread damage which goes unnoticed and can lead to product failure or make removal a daunting task. The screw can also be dropped accidentally into the turret hole and may be very hard to remove (non-magnetic materials).

SUMMARY OF THE INVENTION

It is the intent of this invention to address the aforementioned problems and concerns. The invention is a screwdriver having a special drive end with a non-tamp screw head that is frictionally preassembled into a turret already in screw head engagement. Therefore, the screw, being a mating non-tamp type, is held in its full forward position against a shoulder to prevent shifting. The turret is positioned; and the screw is then tightened and torqued up to a preadjustable torque limit. The driver is then removed. When the screwdriver is reinserted to engage and untighten the screw, the torque limiting feature is locked out to compensate for possible increases in backout torque, thereby permitting screw disengagement while the screwdriver is held axially by friction and the screw itself remains correctly captivated in the turret.

In its simplest form, the present invention provides a driver for captively engaging a fastener for assembling a first part having a shoulder to a mating fitting having an aperture. The driver according to the present invention includes a shaft having a fastener-engaging end, and means for holding the fastener in a full-forward position against the shoulder of the first part during attachment of the fastener to the aperture of the mating fitting. The holding means operably engages between the shaft and the first part.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION OF THE PREFERRED EMBODIMENT

Figure 1:
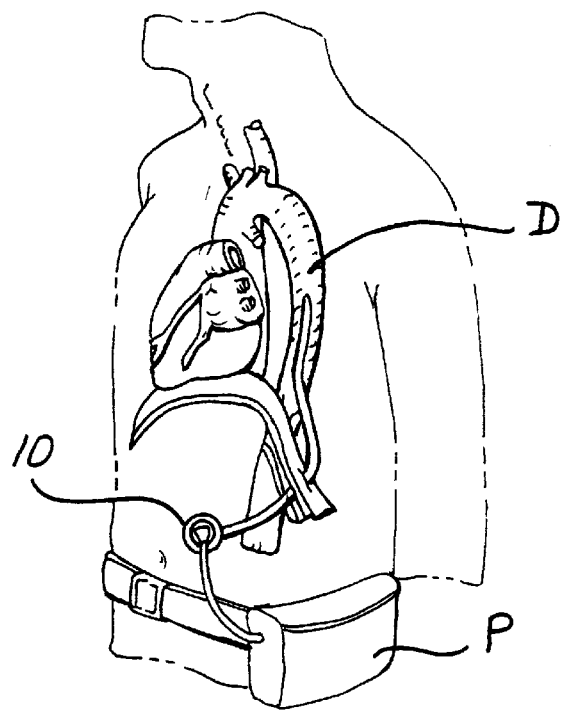
FIG. 1 is a schematic diagram illustrating the PAD device used in combination with an internally implanted device and an external monitoring/control device.
Figure 2:
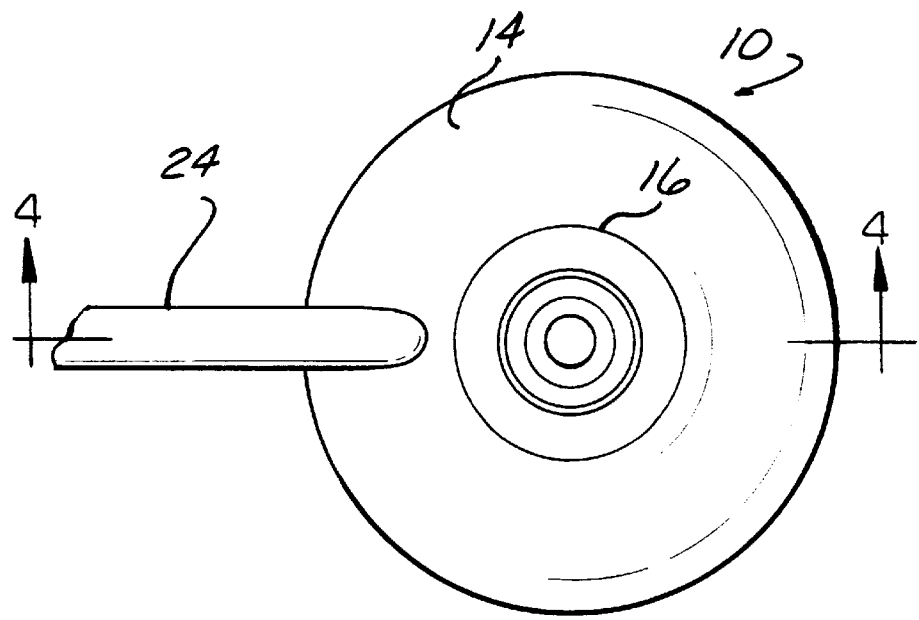
FIG. 2 is a schematic diagram illustrating a top view of the PAD with a removable turret and turret/screwdriver assembly.
Figure 3:
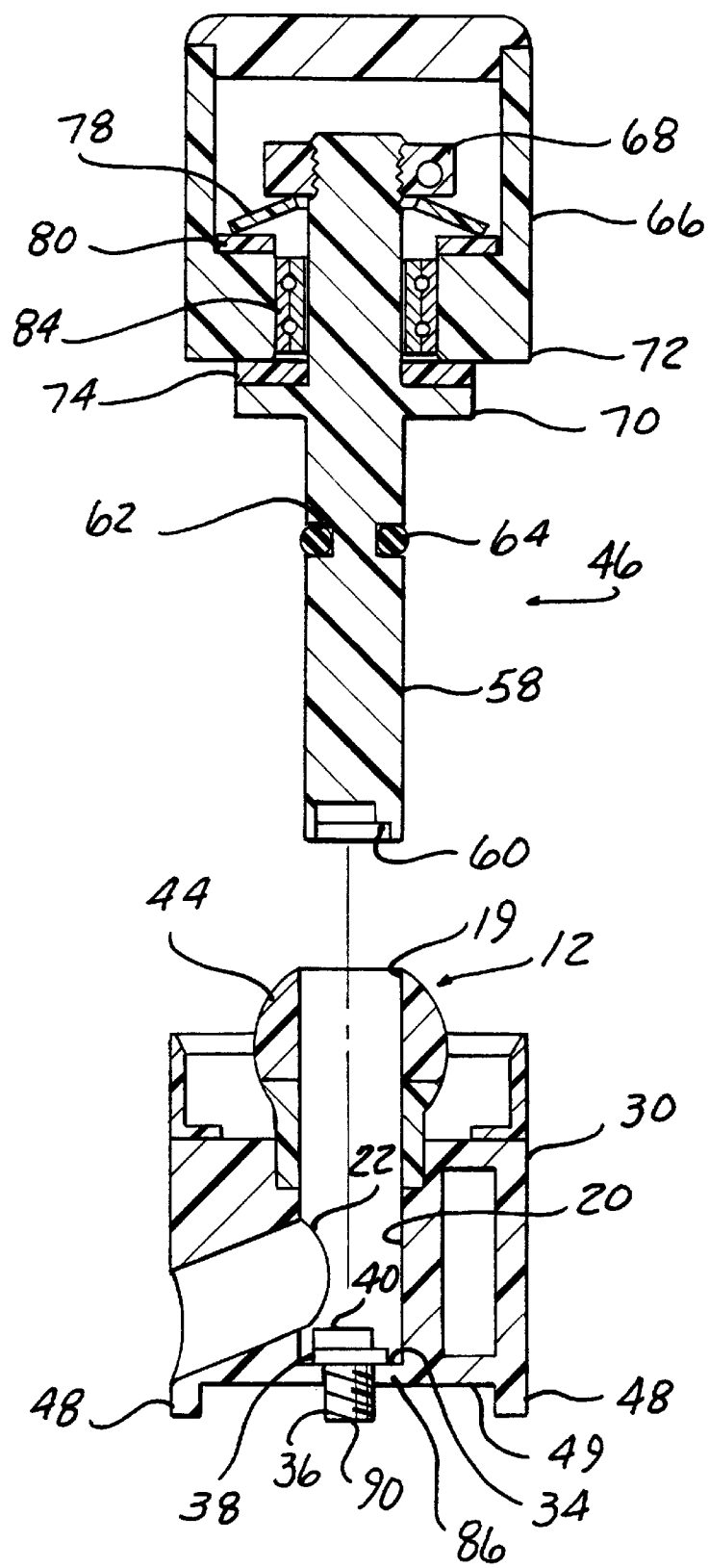
FIG. 3 is a cross sectional view screwdriver disengaged from the turret.
Figure 4:
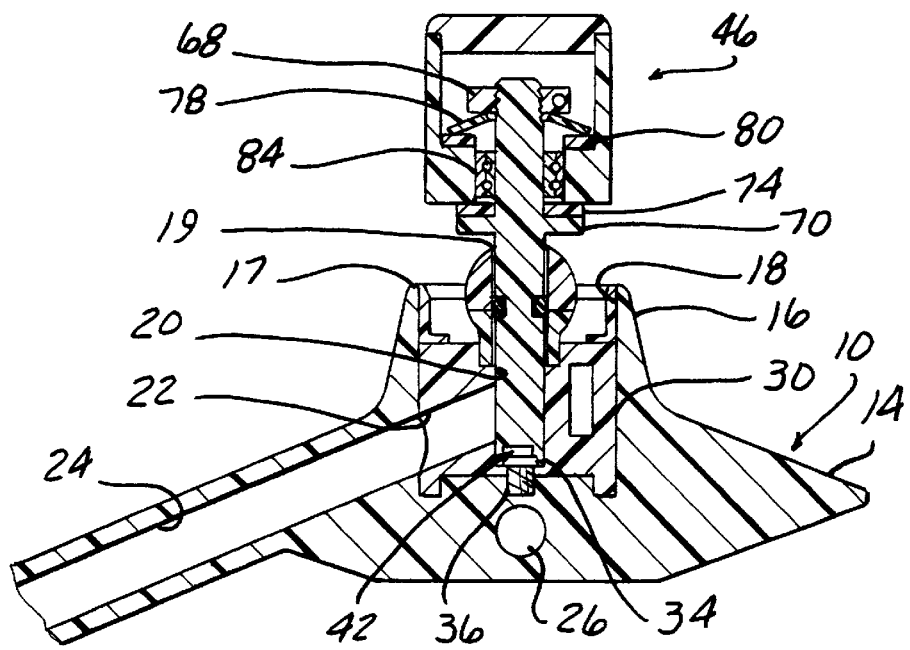
FIG. 4 is a cross sectional view of the device taken on the lines 4—4 of FIG. 2 showing the screwdriver and screw assembled into the turret.

Looking at FIGS. 1–5, a percutaneous access device (PAD) generally comprises a housing 10 and a removable turret assembly 12. As seen in FIG. 1, the housing 10 is implantable beneath the skin of a patient in any suitable manner. The PAD 10 provides fluid contact through the PAD 10 between an associated organ or device D and any external mechanisms or devices such as a pump P. The general type of PAD may be employed, for example, to supply a pneumatic connection and electrocardiogram lead connections to a dynamic aortic patch of the type disclosed in Kantrowitz et al, U.S. Pat. No. 4,051,840. The PAD and removable turret assembly disclosed herein is described in detail in Ser. No. 08/856,905, filed on May 15, 1997, the specification of which is incorporated by reference herein. Generally, the PAD includes a flange body 14 having a generally flat disk shape configuration and an upper wall contiguous with a neck 16 and a lower wall opposed to the upper wall and generally connected therewith. The housing 10 is implanted immediately below the dermal layer at the junction between the dermis and hypodermis. The flange body 14 defines a central interior chamber 18 including at least one fluid conveying channel which facilitates the transfer of fluids such as a gaseous or liquid material through the housing 10 and terminating in an aperture 22 which is capable of providing communication between the exterior of the flange body 14 and the fluid conveying channel in instances in which the PAD is employed with a dynamic aortic patch D. A suitable conduit 24 can be secured to the housing 10 at aperture 22 to provide communication between the corresponding fluid conveying channel in the flange body 14 and the associated device or organ D. The specific conduit 24 can convey gaseous material which controls the inflation and deflation of the associated aortic patch D. In FIG. 4, an auxiliary aperture 26 and associated channel are also provided. This auxiliary aperture 26 and channel can provide access for various electronic monitoring leads, electrical wires or the like i.e. for electrocardiogram monitoring leads, etc. Other apertures can be included in the flange body 14 as necessary. However, it is to be understood that the material conveyed through such conduits can be varied depending on the particular use desired for the PAD. Further, it is understood that the PAD is described as an illustration of a typical use for the screwdriver and turret assembly; but the invention is also beneficial for mechanical and electromechanical assemblies having similar structures.

The neck 16 of the housing 10 defines a hollow interior which communicates with a fluid channel defined in the flange body 14. The hollow interior is accessible through an opening 18. The hollow interior defined in the neck 16 is, preferably, essentially cylindrical and has a predefined internal diameter sufficient to receive the removable turret assembly 12.

The removable turret assembly 12 is adapted to matingly fit within the hollow interior defined by the neck 16 of the housing 10. The turret assembly 12 is removably fastened within the neck by suitable fastening means. The fastening means is preferably contained in the flange body 14 of the housing 10 and will be described in greater detail subsequently.

The turret assembly 12 includes means for providing electric communication through the housing in a manner which provides insulation of electrical current from communication and contact with body tissue surrounding the exterior of the housing 10. The turret assembly 12 also includes means for providing fluid access in communication to the fluid conveying channel 24 in the flange body 14.

The turret assembly 12 includes a turret body 30 configured to be received within the neck 16 of the housing 10. The turret body has a central shaft 20 defining the fluid conveying channel which extends from the aperture 19 located in the upper outwardly facing surface 17 into the central region of the turret body 30. The central shaft 20 is preferably positioned coaxially with the central longitudinal axis of the turret body 30. The central shaft 20 terminates at a blind inner wall 34 located proximate to a lower surface of the exterior of the turret body 30. The shaft 20 extends through to the blind inner wall 34 to matingly receive a screw 36 sealed with a sealer or a gasket (not shown). The screw 36 extends from the blind inner wall 34 through the shaft 20 and into threading engagement with suitable means for securing the turret body 30 into the PAD housing 10. Access to the screw 36 is provided through the aperture 19 in the outwardly facing surface 17 and the associated central shaft 20. This provides access to remove or replace the turret assembly as necessary.

Figure 5:
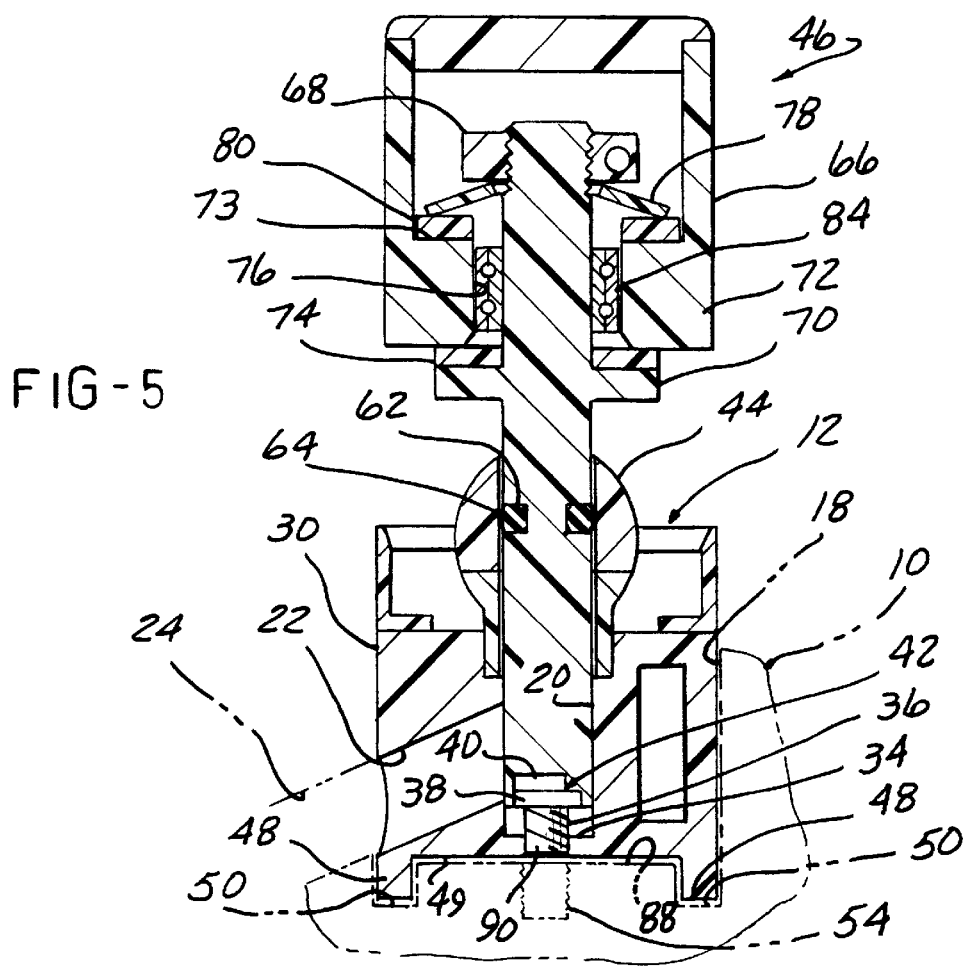
FIG. 5 is the turret and torque screwdriver assembly in the torque position.

The turret 12 nests in the PAD housing 10 so that it bottoms out against the surface of a key and the side branch outlet 22 of the turret 12 is aligned with the side branch outlet 24 of the PAD 10. The key includes a configuration that allows the turret assembly 12 to be placed within the PAD housing 10 in only one unique direction. The key configuration should also include means to prevent the turret assembly 12 from shifting or otherwise moving once installed in the PAD housing 10. In FIG. 5, the key configuration is shown as legs 48 of the turret positioned in complementary grooves 50 of the PAD housing 10.

The screw 36 preferably has a unique configuration that includes a major head diameter 38 and a reduced head diameter 40 eccentric to the major head diameter 38. This creates a customized non-tamp head 42 in which locking torque is transmitted to the head 42 by the known eccentric locking concept. This is only one example of the screw head 42 which may also utilize a special slot, socket or other configuration that does not permit standard screwdrivers, socket drivers or the like to be used. The screw 36 is not held into the turret body 30 by any restraining means and would fall out or shift position with respect to the orientation of the turret at this stage of the assembly. The screw 36 length is limited by the location of the auxiliary aperture 26 for the various electronic monitoring leads. As a result, the handling and removal of the screw 36 in the deep hole within the PAD housing 10 is more difficult.

FIG. 3 shows a view of a tool defining a screwdriver 46 for removal of the screw 36 before engagement into the turret 12. The turret body 30 houses contacts, a current limiter, and an inlet/outlet port 19 for the screwdriver 46 and a branch outlet port for fluid communication to the PAD body. As stated supra, the turret body 30 may be configured to have opposing legs 48 extending from its bottom portion 49 for communicating with complementary grooves 50 located at the end of the central interior chamber 18 in the PAD body 10. The legs and complementary groove configuration form the key to provide accurate installation of the turret body 30 into the PAD body 10. The inlet/outlet port 19 in the upper outwardly facing surface 17 of the turret body 30 forms the channel 20 that extends through the center of turret body 30 and terminates at a centrally located threaded aperture 54. The upper surface of the turret body at the inlet/outlet port 18 incorporates a spherical sealing surface 44 for reasons to be discussed further.

In the Figures, the screwdriver 46 is shown having a shaft 58 that is configured to matingly fit within the channel 20. The shaft 58 of the screwdriver 46 has an eccentric drive socket 60 at its lower end to complement and receive the head 42 of the screw 36. The shaft 58 of the tool or screwdriver 46 has a radially recessed area 62 on its length for receiving an O-ring 64. Spaced above the recessed area 62 on the shaft 58 is a radial flange 70. A handle 66 is secured at the upper portion of the screwdriver shaft 58 by a threaded locking collar 68. The handle 66 rests on the radial flange 70 located on the shaft 58. The handle 66 has a lower shoulder 72 that is positioned such that a slip washer 74 separates the handle shoulder 72 and the radial flange 70. The locking collar 68 compresses a conical washer 78 which in turn places an axial load on a second slip washer 80. The second slip washer 80 is positioned on an upper ledge 73 of the shoulder 72. Therefore, the handle shoulder 72 is compressed between the two slip washers 74 and 80. The washers 74 and 80 may be manufactured from a Delrin AF material or other similar plastic that has a static and dynamic coefficient of friction that have similar values so that breakout torque and slip torque are reasonably close in value. A roller clutch bearing 84 is located on the screwdriver shaft 58 between the two slip washers 74 and 80. Bearing 84 is also disposed between the shaft 58 and an inner radial surface 76 of the shoulder 72 of the handle 66. The locking collar 68 is preadjusted to a predetermined value to provide the proper seating torque to the screw 36 so that the handle 66 slips when this predetermined value is attained. The roller clutch 84 acts as a radial bearing member capable of free axial motion on the shaft 58 to compensate for wear on the slip washer faces.

The screwdriver tool 46 and turret 12 are supplied to the user for complete installation as a single unit. As a unit, the screw 36 has been bottomed out against a shoulder 86 in the blind inner wall 34 at the base of the turret assembly 12 and held in place by the engaged screwdriver shaft 58 within the turret, which is held in place by the O-ring 64.

Looking at FIG. 5, during installation the screwdriver 46 and turret assembly 12 are together pushed into the interior chamber 18 of the PAD housing 10 wherein the opposing legs 48 at the base 49 of the turret engages within the complementary groove 50 of the PAD 10 for a key engagement to provide correct alignment. The complementary groove 50 of the PAD 10 forms an upwardly facing surface 88 therebetween. When the screwdriver 46 and turret assembly 12 are inserted into the body of the PAD 10, the upwardly facing surface 88 pushes the screwdriver 46 and the screw 36 back a distance that is equal to the screw projection beyond the blind inner wall 34 in the base 49 of the turret assembly 12 so that the lower surface 90 of screw 36 portion is flush with the blind inner wall 34 of the turret keyway feature. This position of the screw 36 within the turret is shown in FIG. 5. The screwdriver 46 and screw 36 are held in position within the turret by the friction of the O-ring 64 against the interior fluid channel 20 of the turret assembly 12. The position of screw 36 is controlled by the drive socket 60, the turret pilot aperture 54, and the key surface configuration.

As positioned in FIG. 5, the screw 36 is ready for engagement into the PAD housing 10 by an axial thrust and clockwise rotation of the screwdriver 46. This rotational movement and thrust on the screwdriver 46 overcomes the prevailing O-ring 64 friction so that the screw 36 may be threadingly secured to the PAD housing 10 via the threaded aperture 54. When maximum torque is achieved, the handle 66 rotates with respect to shaft 58 by "slipping" along slip washers 74 and 80 to prevent overtorqueing. When the screw 36 is secured to the PAD housing 10, the screwdriver 46 may then be removed from the turret 12.

To later remove the turret, the screwdriver 46 enters the central bore or channel 20 of the turret assembly 12 and engages the screw 36 therein. The eccentric drive socket 60 of the screwdriver 46 encloses over the non-tamp head 42 of screw 36 so that axial thrust in a counterclockwise rotation of the screwdriver 46 unthreads the screw 36 in the turret assembly 12. The clutch bearing 84 "locks" the handle 66 to the shaft 58 in the counterclockwise direction to permit application of torque greater than the predetermined value to remove the screw 36. Once the screw 36 is unthreaded from threaded slot 54, the entire screwdriver 46 and turret assembly 12 can then be removed from the PAD 10 by pulling on the spherical sealing surface 44 of the turret assembly 12.

Figure 6:
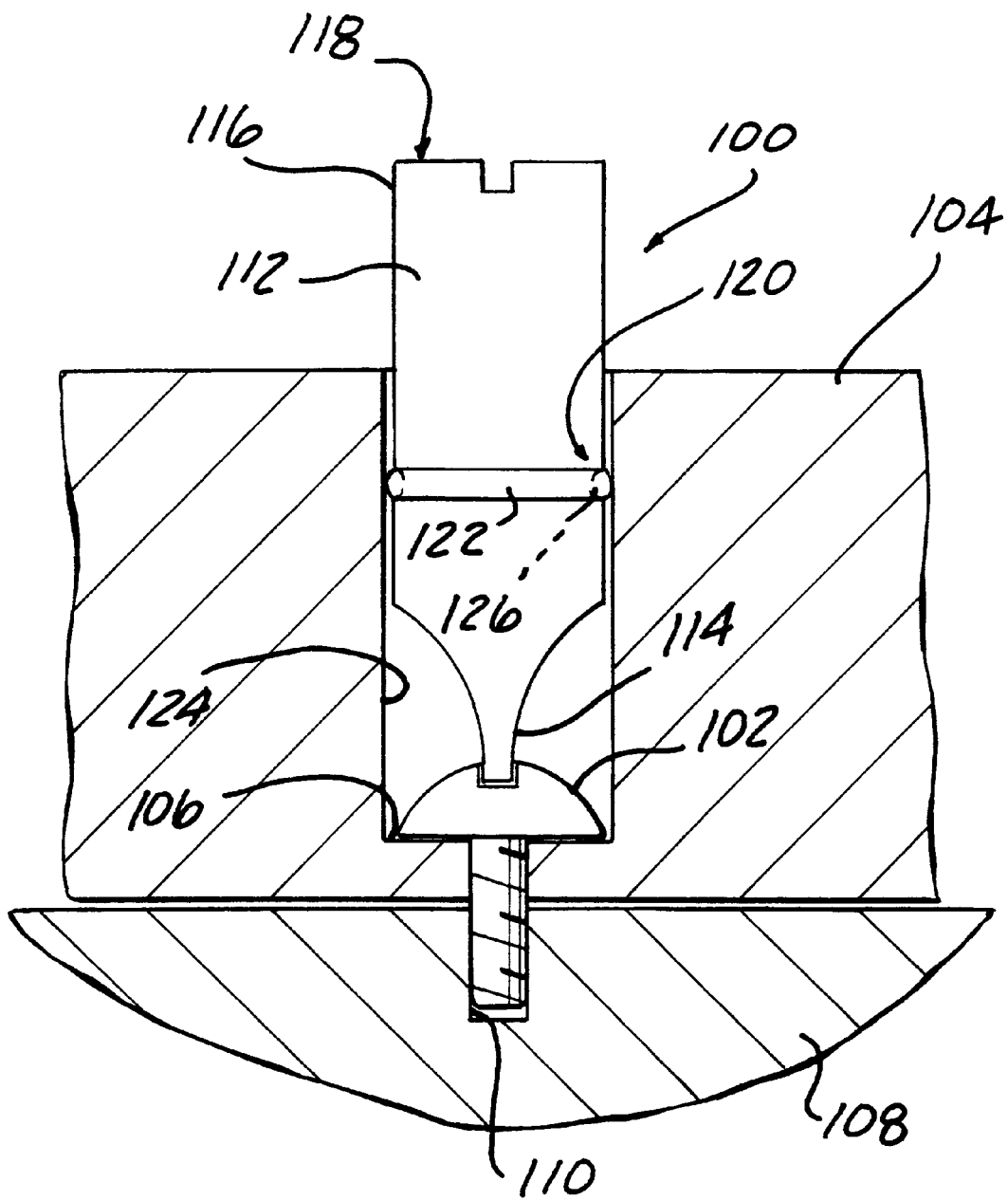
FIG. 6 is a schematic diagram illustrating a driver for engaging a fastener to assemble a first part with respect to a second part according to the present invention.

Referring now to FIG. 6, it is believed that the present invention has numerous applications in addition to the medical example described in detail above. The present invention provides a driver 100 for captively engaging a fastener 102 for assembling a first part 104, having a shoulder 106 to a mating fitting 108, having an aperture 110. The driver 100 can include a shaft 112, having a fastener engaging end 114. The fastener-engaging end 114 of the shaft 112 can include any type of configuration complementary to the head of the fastener. By way of example and not limitation, the fastener-engaging end 114 can take the form of a flat blade screwdriver, Phillips head screwdriver, star screwdriver, Alan wrench driver, hex-head socket, or any other custom or standard configuration. The opposite end 116 of the shaft 112 from the fastener-engaging end 114 can include a handle (seen in FIGS. 4 and 5), or other standard handle configuration, or can include a head 118 for engagement by another manual or powered driver. If the opposite end 116 includes a head 118 for engagement by another driver, the head 118 can be in any standard or custom configuration desired for the particular application. By way of example and not limitation, the head 118 can be in the form of a flat blade screwdriver receiving head, a Philips screwdriver receiving head, an Alan wrench receiving head, a hex-head, a star tool receiving head, or any other standard or custom configuration desired.

Means 120 is provided for holding the fastener 102 in a full forward position against the shoulder 106 of the first part 104 during attachment of the fastener 102 to the aperture 110 of the mating fitting 108. The holding means 120 is operably engageable between the shaft 112 and the first part 104. Preferably, the holding means 120 captively retains the fastener 102 with respect to the first part 104 during an assembly process for connecting the first part 104 to the mating fitting 108. After the assembly process is complete, the driver 100 can be removed from the first part 104. If disassembly of the first part 104 from the mating fitting 108 is required, the driver 100 can be re-engaged with respect to the first part 104 to captively retain the fastener 102 with respect to the first part 104 during the disassembly process. In the preferred configuration illustrated in FIG. 6, the holding means 120 can include an O-ring 122, frictionally engaging a wall 124 of the first part 104. Preferably, the O-ring 122 is engaged on the shaft 112 and retained within a groove 126 formed in the shaft 112. The O-ring 122 advantageously holds the driver 100 and fastener 102 in a predetermined relationship with one another with respect to the first part 104 and resist unintentional removal of the driver 100 and/or fastener 102 from the first part 104. The O-ring 122 permits the driver 100 to be driven rotatably to engage and/or disengage the fastener 102 with respect to the aperture 110 of the mating fitting 108. In addition, the O-ring 122 permits the driver 100 to move with respect to the first part 104 when removal of the driver 100 is desired, and/or to re-engage the driver 100 with the first part 104 in order to disassemble the fastener 102 with respect to the aperture 110 and the mating fitting 108.

The driver 100 can include a handle connected to the shaft 112. The handle can include means for adjusting the maximum torque transmittable from the handle to the fastener 102. As previously illustrated and described with respect to FIGS. 4 and 5, the adjusting means can include a conical washer disposed between a threaded locking collar and a first slip washer set on a shoulder of the handle. The adjusting means can also include a roller clutch bearing disposed on the shaft, and a second slip washer engaging an annular flange on the shaft, such that the roller clutch bearing is positioned between the first and second slip washers, similar to that shown in FIGS. 4 and 5. With a handle similar to that shown in FIGS. 4 and 5, the driver according to the present invention can include means for rotating the shaft 112 with the handle up to a predetermined torque during attachment of the fastener 102 and for locking the handle with respect to the shaft 112 during reverse rotation of the shaft 112 when detaching the fastener 102. The rotating and locking means can include a roller clutch bearing disposed between a portion of the handle and a portion of the shaft. If the shaft 112 is provided with a handle similar to that illustrated in FIGS. 4 and 5, the handle can have an inwardly facing shoulder portion with a first surface and a second surface, where a first slip washer is engageable with the first surface and a second slip washer is disposed between the second surface and a radially outwardly extending flange of the shaft, as can be seen in FIGS. 4 and 5. Preferably, the first and second slip washers are constructed of materials having similar static and dynamic coefficient of friction values. If the shaft 112 is provided with a handle similar to that illustrated in FIGS. 4 and 5, adjustable means can be provided for selectively setting a predetermined seating torque to be applied to the fastener during an assembly process.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A driver for captively engaging a fastener for assembling a first part having a shoulder to a mating fitting having an aperture comprising:

a shaft having a fastener-engaging end;

a handle connected to the shaft;

means for adjusting maximum torque transmittable from said handle to said fastener including a conical washer disposed between a threaded locking collar and a first slip washer set on a shoulder of said handle, wherein the means for adjusting maximum torque further includes a roller clutch bearing annularly disposed on said shaft and a second slip washer set on an annular flange on said shaft, such that said roller clutch is disposed between said first and second slip washers; and means, operably engageable between the shaft and the first part, for holding the fastener in a full forward position against the shoulder of the first part during driving of said fastener with respect to the aperture of the mating fitting.

2. A driver for captively engaging a fastener for assembling a first part having a shoulder defining a transition between an aperture having first and second peripheral walls to a mating fitting having an aperture comprising:

a shaft having a fastener-engaging end;

means, operably engageable between the shaft and one of said first and second peripheral walls of the first part, for holding the fastener in a full forward position against the shoulder of the first part during driving of said fastener with respect to the aperture of the mating fitting; and means for rotating said shaft with a handle up to a predetermined torque during attachment of said fastener and for locking said handle with respect to said shaft during reverse rotation of said shaft when detaching said fastener.

3. The driver of claim 2, wherein the rotating and locking means further comprises a roller clutch bearing disposed between a portion of said handle and a portion of said shaft.

4. The driver of claim 2, further comprising:

said handle having an inwardly facing shoulder portion, the shoulder portion having a first surface and a second surface;

a first slip washer engageable with the first surface of the shoulder portion of the handle; and said shaft having an outwardly extending radial flange for supporting the second surface of the shoulder portion; and a second slip washer disposed between said radial flange and said second surface of said shoulder portion of said handle.

5. The driver of claim 4, wherein the first and the second slip washers are constructed of materials having similar static and dynamic coefficient of friction values.

6. The driver of claim 2 further comprising adjustable means for providing a preselected seating torque to said fastener.

* * * * *